United States Patent
Higgins, Jr. et al.

(10) Patent No.: US 7,090,491 B2
(45) Date of Patent: Aug. 15, 2006

(54) SINGLE-DOSE DENTAL ADHESIVE DELIVERY SYSTEM AND METHOD

(75) Inventors: Stephen R. Higgins, Jr., Foothill Ranch, CA (US); Daniel Ng, Wildomar, CA (US)

(73) Assignee: Kerr Corporation, Orange, CA (US)

( * ) Notice: Subject to any disclaimer, the term of this patent is extended or adjusted under 35 U.S.C. 154(b) by 268 days.

(21) Appl. No.: 10/292,206

(22) Filed: Nov. 12, 2002

(65) Prior Publication Data

US 2004/0089372 A1 May 13, 2004

(51) Int. Cl.
*A61C 17/00* (2006.01)
(52) U.S. Cl. .......................... 433/80; 401/118; 401/129
(58) Field of Classification Search ................. 433/80, 433/89, 90; 206/361; 401/118, 129; 222/145.5
See application file for complete search history.

(56) References Cited

U.S. PATENT DOCUMENTS

| | | | | |
|---|---|---|---|---|
| 5,464,348 A | * | 11/1995 | Fischer et al. ............... | 433/26 |
| 5,860,806 A | | 1/1999 | Pranitis, Jr. et al. .......... | 433/80 |
| 6,082,999 A | * | 7/2000 | Tcherny et al. ............... | 433/80 |
| 6,328,159 B1 | | 12/2001 | Discko, Jr. ................... | 206/229 |
| 6,372,816 B1 | | 4/2002 | Walz et al. ................... | 523/116 |
| 6,450,717 B1 | * | 9/2002 | Salz et al. .................... | 401/125 |
| 6,612,465 B1 | * | 9/2003 | Pierson et al. ................ | 222/82 |
| 6,719,729 B1 | * | 4/2004 | Sogaro ......................... | 604/191 |
| 2002/0027088 A1 | | 3/2002 | Discko, Jr. ................... | 206/229 |
| 2002/0044816 A1 | * | 4/2002 | Strauss ........................ | 401/123 |
| 2002/0154936 A1 | * | 10/2002 | Muller ......................... | 401/130 |

FOREIGN PATENT DOCUMENTS

EP 1 205 196 A1 5/2002

OTHER PUBLICATIONS

3M™ ESPE™, *Etch, Prime, Bond, All-In-One, All in Seconds*, Product Advertisement, Dental Economics, Nov. 2001, 1 pp.
Kerr Corporation, *To Etch or Not to Etch? That is No Longer The Question*, Brochure, OptiBond® Solo Plus Self-Etch Primer, 2002, 2 pp.
3M™, *3M™ ESPE™ Direct Light-Cure Restorative Prompt L-POP™ All-In-One Adhesive*, Product Bochure, 2002, 2 pp.
Ivoclar Vivadent AG—Products, *EXCITE®*, Website www.ivoclarvivadent.us.com, 2002, 2 pp.

* cited by examiner

*Primary Examiner*—Cary E. O'Connor
(74) *Attorney, Agent, or Firm*—Wood Herron & Evans, LLP

(57) ABSTRACT

A dispenser has first and second reservoirs configured to contain first and second components of a single dose of a multi-component dental adhesive. The reservoirs are sealed by closures which are slidably received in the reservoirs. When the closures are moved from first positions to second positions, the contents of the reservoirs may be accessed with an adhesive applicator. An applicator configured to be used with the dispenser has a collar spaced from a tip of the applicator, whereby the applicator may be used to move the closures while ensuring that the tip does not contact the closures.

12 Claims, 2 Drawing Sheets

SINGLE-DOSE DENTAL ADHESIVE DELIVERY SYSTEM AND METHOD

FIELD OF THE INVENTION

The present invention relates to delivery of dental adhesives, and more particularly to a dispenser for delivering two-part dental adhesives in a single-dose quantity.

BACKGROUND OF THE INVENTION

The application of dental restorations to the teeth of patients requires the use of specially formulated dental adhesives that will be effective to form a bond with a surface of the patient's dental anatomy. The more effective of the adhesives currently having the most widespread use include resins that are applied to a tooth surface, for example, and then cured with ultraviolet or visible light. With certain formulations of such light cure adhesives, a small amount of such light is sufficient to start an adhesive curing reaction that will propagate through the entire dose of adhesive. Other types of adhesives require larger exposures to such light for the cure of the entire body of the adhesive. Such adhesives are used for the bonding of more transparent or semi-transparent restorations, such as direct restorations, veneers and other thin, small or in situ formed composite restorations.

The more effective of the dental adhesives for the uses discussed above have been provided to dentists in multiple parts. The various parts of these multi-part adhesive systems take advantage of the different properties at different parts of the system at the different stages of their use. A first part of the system may include, for example a primer, which is painted onto an area of the tooth to which the restoration is to be attached. The primer dries the surface and penetrates to form a basis for an effective bond. A second part may include a filled or an unfilled resin that is applied over the first part to interact with it and form a bond. In some forms, the second part is itself supplied in two parts. In a superior form a subpart of the second part is a resin and the other subpart is a fill material in the form of minute glass beads. The fill, which is mixed to a content of about 48% of the mixture with the resin, contributes strength and shock absorbency to the bond. Multi-part adhesives of this type are available in an alcohol base and marketed under the trademarks Optibond and Optibond FL by Kerr Dental Materials Center of Orange, Calif.

The application of each part of the multi-part adhesive system by a dentist calls for the coating of a small area of a patient's tooth, for example, with a small quantity of each part of the adhesive system being applied. The coating with each adhesive part is followed by the placement of the restoration, which may be a restoration formed in a dental laboratory on a model of the patient's teeth that is transferred by the dentist onto the patient's dental anatomy or may be a restoration formed in situ by the dentist, usually from a composite material. The different parts of the multi-part adhesive systems are traditionally packaged in containers designed to hold a quantity of material sufficient for bonding multiple restorations and which can be resealed after each use. In a one part adhesive, a single container designed to hold a quantity of material sufficient for bonding multiple restorations in the treatment of multiple patients and which can be resealed after each use is used. To use such containers, the dentist or dental assistant is required to retrieve the containers for each part of the adhesive system from a storage area, open each container, dispense from each container into another container (typically a container which constitutes an open well) the required amount of the adhesive part being dispensed, reseal each container for each adhesive part and return the containers to the storage area.

To reduce the time and effort associated with administering adhesives provided in bulk containers, adhesive dispensers having pre-measured doses of adhesives have been developed. Prior art dispensers for delivering pre-measured doses of dental adhesives for use by a practitioner have been provided as trays or pouches having one or more wells for containing the adhesive components and an applicator which is partially secured within the tray or pouch. One example of this type of dispenser is shown in U.S. Pat. No. 6,328,159 to Discko, Jr. In these types of dispensers, the applicator may be removed from the dispenser by prying the cover off using the applicator for leverage, whereby the wells containing the adhesive components may be accessed with the applicator. Alternatively, the adhesive components may be squeezed from the adhesive-containing wells to an applicator well whereafter the applicator is pulled from the dispenser to apply the adhesive. One drawback of these types of dispensers is that the applicator tip may be damaged when the applicator is used to remove the cover from the dispenser to expose the adhesive wells. On the other hand, when the adhesive wells are squeezed to extrude the adhesive components into an applicator well, not all of the components may be dispensed into the applicator well, resulting in wasted adhesive. Moreover, when the dispenser cover is removed to expose the adhesive wells, the adhesive components are exposed to the environment, thereby increasing the potential for contamination.

There is thus a need for an adhesive dispenser which can be used to dispense a single dose of dental adhesive having one or more components and which overcomes drawbacks of the prior art, such as those discussed above.

SUMMARY OF THE INVENTION

The present invention provides a dispenser which may be used to dispense pre-measured doses of a multi-part dental adhesive and which minimizes exposure of the adhesive components and ensures that substantially all of the adhesive components may be dispensed using an applicator. In one exemplary embodiment, the dispenser includes first and second reservoirs which are configured to individually contain first and second adhesive components of the multi-part dental adhesive. First and second closures associated with the first and second reservoirs are movable from first positions where the reservoirs are sealed to second positions where the contents of the reservoirs may be accessed with an applicator. In an exemplary embodiment, the first and second closures are piston-like members, which are sized to fit slidably within the first and second reservoirs. The closures have apertures which are configured to communicate with the reservoirs when the closures are moved to the second position whereby the contents of the reservoirs may be accessed through orifices and passages of the closure which are in fluid communication with the apertures.

In another aspect of the invention, an applicator for use with the dispenser has a collar provided on a handle portion of the applicator near the applicator tip. Advantageously, the collar is spaced from the tip so that the collar may be used to move the closures from the first positions to the second positions and thereby permit access the reservoirs with the applicator without damaging the tip.

In another aspect of the invention, a kit for dispensing a multi-component dental adhesive includes a dispenser having first and second reservoirs configured to contain first and second components of the dental adhesive, first and second closures associated with the first and second reservoirs whereby the contents of the reservoirs may be accessed by moving the closures from first positions to second positions, and an applicator having a collar spaced from a tip of the applicator whereby the collar may be used to engage the closures to move them from the first positions to the second positions. In an exemplary embodiment, the kit may further include a third adhesive component which is provided in a separate container. The third adhesive component may be added to one of the first and second reservoirs for mixing with the contents of the reservoir prior to administering the adhesive.

In yet another aspect of the invention, a method of dispensing a multi-component dental adhesive includes the steps of engaging a first closure on a dispenser to access a first reservoir associated with the closure, inserting an applicator into the reservoir to access a first component of the dental adhesive, applying the first component of the dental adhesive to a target, engaging a second closure on the dispenser with an applicator to access a second reservoir associated with the second closure, inserting the applicator into the second reservoir to access a second component of the dental adhesive, and applying the second component of the dental adhesive to the target.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
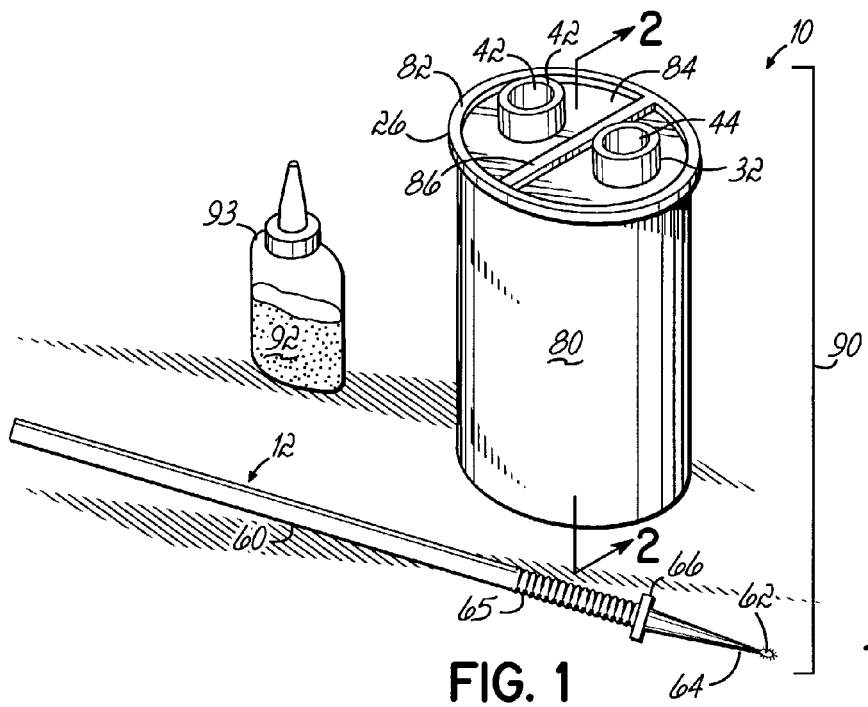
FIG. 1 is a perspective view of an exemplary adhesive dispenser and applicator according to the present invention.
Figure 2:
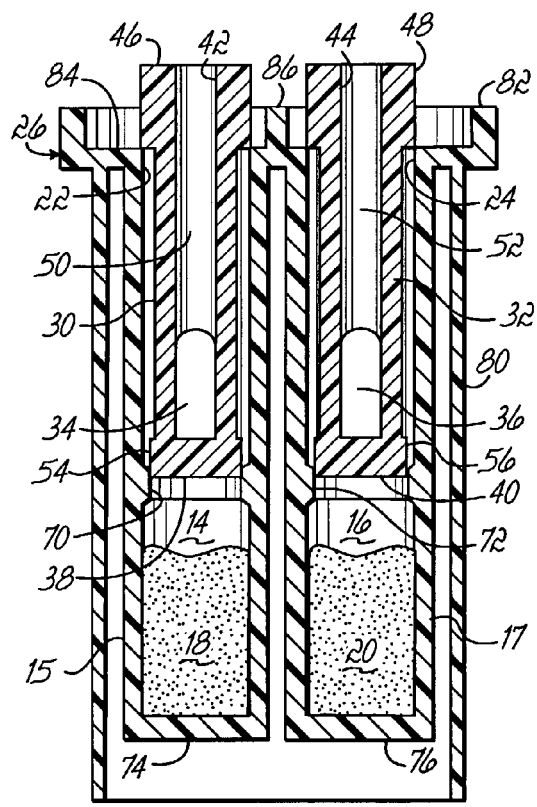
FIG. 2 is a cross-sectional view of the adhesive dispenser of FIG. 1 taken along line 2—2.

Referring to FIG. 1, there is shown an exemplary dispenser 10 and an exemplary applicator 12 according to the present invention. With further reference to FIG. 2, the dispenser 10 includes first and second reservoirs 14, 16 containing at least first and second components 18, 20 of a dental adhesive. In the exemplary embodiment shown, the first and second reservoirs 14, 16 are elongate tubular members defined by sidewalls 15, 17, bottom walls 74, 76 adjacent the sidewalls 15, 17, and having openings 22, 24 opposite the bottom walls 74, 76 to permit access to the respective reservoirs 14, 16. While reservoirs 14, 16 are depicted as tubular members having a single sidewall, it will be recognized that the reservoirs 14, 16 may be formed of other shapes and may have more than a single sidewall.

The dispenser 10 further includes first and second closures 30, 32 which are slidably received within the first and second reservoirs 14, 16. The closures 30, 32 are moveable between first positions (depicted in FIG. 2) where the closures 30, 32 seal the respective reservoirs 14, 16 and second positions (depicted in FIG. 4 for second closure 32) where the contents of the respective reservoirs 14, 16 may be accessed through their openings 22, 24.

In the exemplary embodiment shown, the closures 30, 32 are generally piston-shaped members sized to fit frictionally within the respective reservoirs 14, 16. Each closure 30, 32 has a first end 38, 40 which faces the bottom wall 74, 76 of the respective reservoir 14, 16 in which it is received and a second end 46, 48 opposite the first end 38, 40. The closures 30, 32 have sealing portions 54, 56 at the first ends 38, 40 and orifices 42, 44 at the second ends 46, 48. Apertures 34, 36 are provided at a distance intermediate the sealing portions 54, 56 and the second ends 46, 48 and communicate with respective orifices 42, 44 by passages 50, 52 extending therebetween. The closures 30, 32 are independently moveable within their respective reservoirs 14, 16 such that the contents of a given reservoir 14, 16 may be accessed through the orifices 42, 44, passages 50, 52, and apertures 34, 36 when the closures 30, 32 are moved from first positions to the second positions.

In an exemplary embodiment, one of the closures 30, 32 may be configured such that it is visually distinct from the other closure whereby a user can distinguish the closures 30, 32 to correctly identify a desired reservoir 14, 16. For example, one of the reservoirs 14, 16 may be configured to have a color which is distinguishable from the other closure. Furthermore, because the closures 30, 32 are independently movable and must be moved to the second position to access the contents of a reservoir 14, 16, a user can easily determine by visual inspection of the dispenser 10 whether a given dispenser 10, or even a given reservoir 14, 16 has been previously accessed.

Figure 3:
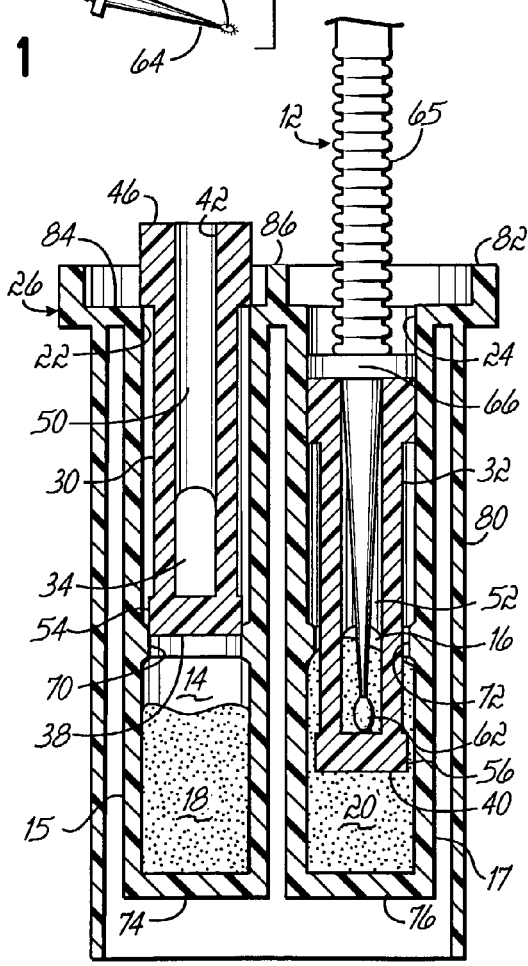
FIG. 3 is a cross-sectional view similar to FIG. 2 and illustrating the use of an applicator to access the contents of the dispenser.
Figure 4:
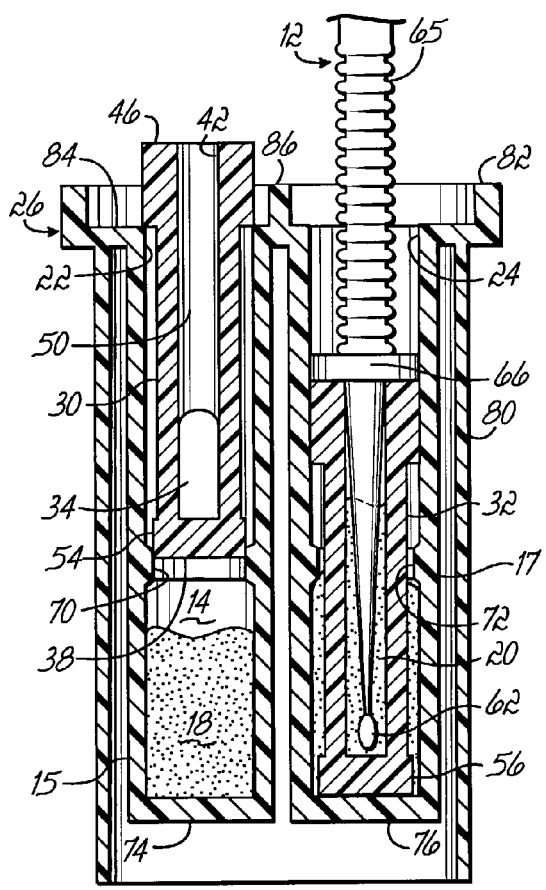
FIG. 4 is a cross-sectional view similar to FIG. 3, depicting the applicator fully inserted into the dispenser.

With reference to FIGS. 3–4, operation of the dispenser 10 will be described with respect to second reservoir 16 and its associated closure 32. It will be understood the first reservoir 14 and first closure 30 operate in a similar manner. As closure 32 is moved from the first position to the second position, the adhesive component 20 contained in the reservoir 16 is displaced by the closure 32 and moves upward around the closure 32 and through the aperture 36 into the passage 52. As also shown in FIGS. 3 and 4, the closure 32 may be moved from the first position to the second position using the exemplary applicator 12 of the present invention. As shown most clearly in FIG. 1, the applicator 12 includes an elongate handle 60 and an applicator tip 62 disposed on a distal end 64 of the handle 60. The handle 60 may have a portion of its length shaped to provide a grip 65 for the applicator 12. The applicator tip 62 is configured to receive adhesive from the dispenser 10 and transfer the adhesive to a desired surface. The applicator 12 further includes a collar 66 spaced from the applicator tip 62 along the length of the handle 60. Advantageously, the collar 66 engages the second end 48 of the closure 32 when the tip 62 is inserted through the orifice 44 and into the passage 52 of the closure 32. The applicator 12 may then be used to move the closure 32 from the first sealed position to the second position wherein the adhesive component 20 may be accessed by the applicator tip 62. In an exemplary embodiment, the spacing between the applicator tip 62 and the collar 66 along the length of the handle 60 is selected so that the applicator tip 62 will not bottom out against the first end 40 of the closure 32. Such bottoming out is undesirable because contact with the first end 40 of the closure 32 could deform or otherwise damage the applicator tip 62.

The dispenser 10 further includes seals 70, 72 disposed within the reservoirs 14, 16 and configured to engage the closures 30, 32 to thereby seal off the reservoirs 14, 16 from the outside environment. In the exemplary embodiment shown, the seals 70, 72 are annular protrusions formed on the interior portions of sidewalls 15, 17 and located intermediate the openings 22, 24 and bottom walls 74, 76 of the reservoirs 14, 16. Advantageously, the sealing portions 54, 56 of closures 30, 32 engage the seals 70, 72 when closures 30, 32 are in the first positions such that the apertures 34, 36 are located within the reservoirs 14, 16, but cannot communicate with the sealed adhesive components 18, 20. As the closures 30, 32 are moved from the first positions to the second positions, the sealing portions 54, 56 disengage the seals 70, 72 and the apertures 34, 36 move past the seals 70, 72 to permit the displaced adhesive component 18, 20 to enter the passages 50, 52 through the apertures 34, 36.

With continued reference to FIGS. 1–4, the exemplary dispenser 10 may further include a housing 80 which encloses at least a portion of the reservoirs 14, 16. In the exemplary embodiment, the housing 80 is in the form of a skirt, or shroud, which surrounds the lengthwise portions of the reservoirs 14, 16, but it will be understood that the housing 80 may assume other configurations. The dispenser 10 may further include a raised rim 82 near a first end 26 of the dispenser 10 to form a well 84 which surrounds the openings 22, 24 of the reservoirs 14, 16. The dispenser 10 may further include a partition 86 formed on the first end 26 of the dispenser 10 intermediate the first and second reservoirs 14, 16, whereby the well 84 may be separated into distinct portions.

In another exemplary embodiment, the dispenser 10 may be packaged together with the exemplary applicator 12 to form a kit 90 for dispensing a multi-component dental adhesive, as depicted in FIG. 1. Advantageously, the kit 90 may include first and second adhesive components 18, 20 disposed in the first and second reservoirs 14, 16. In an exemplary embodiment, the first and second adhesive components 18, 20 may be provided in an amount which is convenient for single-dose application. For example, the adhesive components may be provided in an amount of approximately 0.1 ml to 1.0 ml.

Figure 5:
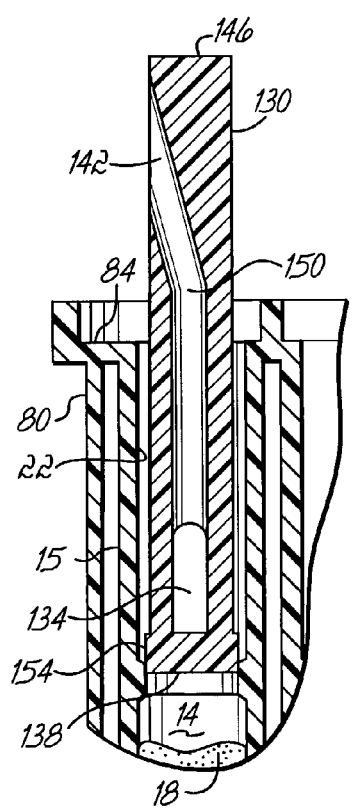
FIG. 5 is a partial cross-sectional view depicting an alternate exemplary closure of the present invention.
Figure 6:
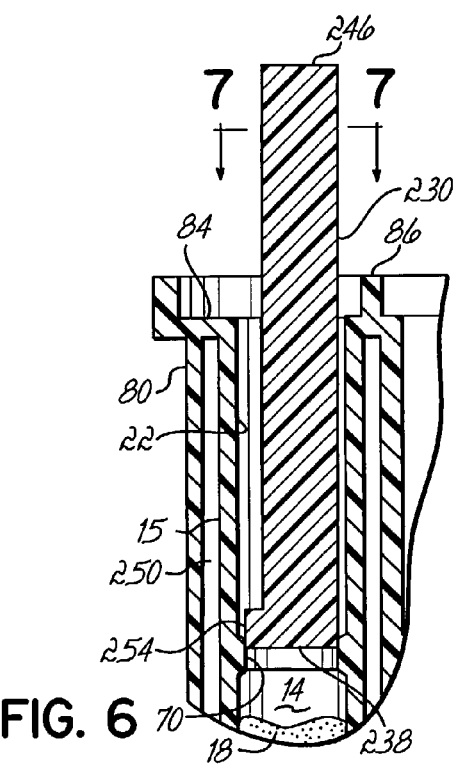
FIG. 6 is a partial cross-sectional view depicting another alternate exemplary closure of the present invention.

FIGS. 5 and 6 depict other exemplary embodiments of closures 130 and 230 according to the principles of the present invention. In these figures, components similar to components of FIGS. 1–4 are similarly numbered. Referring to FIG. 5, there is shown a closure 130 slidably disposed within the first reservoir 14. Closure 130 is similar to closure 30, but has a passage 150 extending between a sealing portion 154 at a first end 138 and an orifice 142 which is located near a second end 146 of the closure. Orifice 142 is spaced from the second end 146 a distance which permits access to the first reservoir 14 from a location exterior of opening 22 when closure 130 has been moved to the second position. Aperture 134 is located between sealing portion 154 and orifice 142, and communicates with orifice 142 by passage 150.

Figure 7:
FIG. 7 is a cross-sectional view of the closure of FIG. 6, taken along line 7—7.
Figure 8:
FIG. 8 is a cross-sectional view of an alternative closure, similar to FIG. 7.

FIG. 6 depicts an exemplary closure 230 wherein a passage 250 is formed between the sidewall 15 of the first reservoir 14 and a flat sidewall 200 which has been formed into the piston-shaped closure 230, between a sealing portion 254 at a first end 238 and a second end 246 of the closure 230. In this embodiment, the contents of the reservoir 14 may be accessed through passage 250 from a location exterior of opening 22 when closure 230 is moved to the second position to urge sealing portion 254 out of engagement with seal 70. FIG. 7 more clearly depicts the cross-sectional shape of closure 230 and flat sidewall 200. It will be understood that various other configurations of closure 230 may be employed to create a passage 250 between sidewall 15 of reservoir 14 and closure 230. For example, a curved sidewall 200a as depicted in FIG. 8 may be formed along closure 230 between sealing portion 254 and the second end 246 to create passage 250.

In another exemplary embodiment, a method of dispensing a multi-component dental adhesive includes the steps of engaging a first closure 30 on a dispenser 10 with an applicator 12 to move the closure 30 to a position which permits access to a first reservoir 14 associated with the closure 30, inserting the applicator 12 into the first reservoir 14 to access a first component 18 of a dental adhesive, applying the first component 18 to a desired target, engaging a second closure 32 on a dispenser 10 with the applicator 12 and move the second closure 32 to a position which permits access to a second reservoir 16, inserting the applicator 12 into the second reservoir 16 to access a second component 20 of the dental adhesive, and applying the second component 20 to a desired target. Accordingly, kit 90 may further include third adhesive component 92 provided in container 93.

In addition to dispensing a two-part adhesive, the dispenser 10 of the present invention could also be used to dispense a three-component adhesive whereby a third adhesive component 92 is provided in a separate container 93 to be added to one of the first or second reservoirs 14, 16 so that the third component 92 can be mixed with one of the first and second components 18, 20 prior to dispensing the adhesive components 18, 20 to a target. For example, the third component 92 may be a liquid which is added to one of the reservoirs 16 through the orifice 44 in the closure 32 after it has been moved from the first sealed position to the second position. After the third component 92 has been added to the reservoir 16, the applicator 12 may be inserted into the reservoir 16 and manipulated to mix the components 20, 92 prior to applying the mixed components to a desired target. Accordingly, kit 90 may include the third adhesive component 92 provided in container 93, as depicted in FIG. 1.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A dispenser for supplying a single dose of a multi-component dental adhesive, the dispenser comprising:
   a dispenser body having formed therein first and second reservoirs sized to contain first and second components of the single dose of dental adhesive, respectively, each of said reservoirs defined by at least one sidewall, a bottom wall adjacent said sidewall, and an opening opposite said bottom wall;

first and second seals associated with said first and second reservoirs, respectively, and disposed on interior portions of said sidewalls intermediate said openings and said bottom walls; and first and second closures slidably received within said first and second reservoirs, respectively, each closure having a first end facing said bottom wall of said reservoir, a second end opposite said first end, a sealing portion proximate said first end, and a passage extending along said closure intermediate said sealing portion and said second end;

said first and second closures movable within said respective first and second reservoirs between first positions wherein their respective sealing portions are spaced from their respectively associated reservoir bottom walls and engage their respectively associated seals to define first and second sealed volumes within said first and second reservoirs, first and second components of the single dose of dental adhesive located within said first and second sealed volumes, respectively, and second positions wherein their respective sealing portions are moved out of engagement with their respectively associated seals toward their respectively associated reservoir bottom walls such that their respectively associated passages are placed in fluid communication with said respective first and second components of the dental adhesive to permit access to said first and second components via said passages in said first and second closures, respectively, from a location exterior of said openings of said first and second reservoir;

wherein said first and second closures are independently movable within said respective reservoirs.

2. The dispenser of claim 1, wherein said first and second closures further include:

an orifice at said second end; and at least one aperture intermediate said second end and said sealing portion;

said passage extending between said aperture and said orifice whereby said orifice is placed in fluid communication with said dental adhesive component through said passage and said aperture when said closure is moved from said first position to said second position.

3. The dispenser of claim 1, wherein said first and second seals comprise annular protrusions formed on said sidewalls.

4. The dispenser of claim 1, further comprising a raised rim proximate said openings of said first and second reservoirs and defining a well which surrounds said openings.

5. The dispenser of claim 4, further comprising a partition formed in said well and separating said openings of said first and second reservoirs.

6. The dispenser of claim 1, wherein one of said first and second closures is visually distinct from the other of said closures to permit identification of said first and second reservoirs associated with said closures.

7. The dispenser of claim 6, wherein one of said closures has a color distinguishable from the other of said closures.

8. A kit for dispensing a single dose of a multi-component dental adhesive comprising:

a dispenser, comprising:

a dispenser body having formed therein first and second reservoirs sized to contain first and second components of the single dose of dental adhesive, respectively, each of said reservoirs defined by at least one sidewall, a bottom wall adjacent said sidewall, and an opening opposite said bottom wall;

first and second seals associated with said first and second reservoirs, respectively, and disposed on interior portions of said sidewalls intermediate said openings and said bottom walls;

first and second closures slidably received within said first and second reservoirs, respectively, each closure having a first end facing said bottom wall of said reservoir, a second end opposite said first end, a sealing portion proximate said first end, and a passage extending along said closure intermediate said sealing portion and said second end;

said first and second closures independently movable within said respective first and second reservoirs between first positions wherein their respective sealing portions are spaced from their respectively associated reservoir bottom walls and engage their respectively associated seals to define first and second sealed volumes within said first and second reservoirs, first and second components of the single dose of dental adhesive located within said first and second sealed volumes, respectively, and second positions wherein their respective sealing portions are moved out of engagement with their respectively associated seals toward their respectively associated reservoir bottom walls such that their respectively associated passages are placed in fluid communication with said respective first and second components of the dental adhesive to permit access to said first and second components at locations adjacent or below said first and second seals via said passages in said first and second closures, respectively, while maintaining said first and second components separate from one another; and an applicator having an applicator tip, an elongate handle portion, and a collar disposed on said handle portion proximate said applicator tip and spaced from said applicator tip a distance which permits said collar to engage one of said closures to move said closure from said first portion to said second position and thereby access a respective reservoir with said applicator tip.

9. The kit of claim 8, further comprising:

a third adhesive component provided in a separate container and configured to be added to one of said first and second reservoirs for mixing with said first or second adhesive components.

10. A method of dispensing a multi-component dental adhesive, comprising:

engaging a first closure on a dispenser with an applicator to move the first closure to a position which permits access to a first reservoir associated with the closure;

inserting the applicator in the first reservoir to access a first component of the dental adhesive with a tip of the applicator;

applying the first component to a desired target;

engaging a second closure on a dispenser with the applicator to move the second closure to a position which permits access to a second reservoir associated with the closure;

inserting the applicator in the second reservoir to access a second component of the dental adhesive with a tip of the applicator; and applying the second component to a desired target.

11. The method of claim 10, further comprising:
adding a third component to one of the first and second reservoirs to combine the third component with one of the first and second components.

12. A dispenser for supplying a single dose of a multi-component dental adhesive, the dispenser comprising:
a dispenser body having formed therein first and second reservoirs sized to contain first and second components of the single dose of dental adhesive, respectively, each of said reservoirs defined by at least one sidewall, a bottom wall adjacent said sidewall, and an opening opposite said bottom wall;
first and second seals associated with said first and second reservoirs, respectively, and disposed on interior portions of said sidewalls intermediate said openings and said bottom walls; and
first and second closures slidably received within said first and second reservoirs, respectively, each closure having a first end facing said bottom wall of said reservoir, a second end opposite said first end, a sealing portion proximate said first end, and a passage extending along said closure intermediate said sealing portion and said second end;
said first and second closures independently movable within said respective first and second reservoirs between first positions wherein their respective sealing portions are spaced from their respectively associated reservoir bottom walls and engage their respectively associated seals to define first and second sealed volumes within said first and second reservoirs, first and second components of the single dose of dental adhesive located within said first and second sealed volumes, respectively, and second positions wherein their respective sealing portions are moved out of engagement with their respectively associated seals toward their respectively associated reservoir bottom walls such that their respectively associated passages are placed in fluid communication with said respective first and second components of the dental adhesive to permit access to said first component at a location adjacent or below said first seal through said passage in said first closure, and to said second component at a location adjacent or below said second seal through said passage in said second closure, respectively, from a location exterior of said openings of said first and second reservoirs.

* * * * *

UNITED STATES PATENT AND TRADEMARK OFFICE
CERTIFICATE OF CORRECTION

PATENT NO. : 7,090,491 B2  Page 1 of 1
APPLICATION NO. : 10/292206
DATED : August 15, 2006
INVENTOR(S) : Higgins, Jr. et al.

It is certified that error appears in the above-identified patent and that said Letters Patent is hereby corrected as shown below:

IN THE SPECIFICATION
Title page, Col. 2, reads "Wood Herron & Evans, LLP" and should read -- Wood, Herron & Evans, LLP -- .
Col. 1, line 33, reads "…system may include, for example a primer, which is painted onto…" and should read -- …system may include, for example, a primer which is painted onto… -- .
Col. 2, line 64, reads "…thereby permit access the reservoirs with…" and should read -- …thereby permit access to the reservoirs with… -- .
Col. 5, line 67, reads "…which has been farmed…" and should read -- …which has been formed… -- .
Col. 6, line 24, reads "…and move the second closure 32 to…" and should read -- …to move the second closure 32 to… -- .
Col. 6, line 59, reads "…spirit of Applicant's general inventive concept." and should read -- spirit of Applicants' general inventive concept. -- .

IN THE CLAIMS
Col. 8, line 41, Claim 8, reads "...move said closure from said first portion to said second position and thereby access..." and should read -- …move said closure from said first position to said second position and thereby access… -- .

Signed and Sealed this

Second Day of January, 2007

JON W. DUDAS
*Director of the United States Patent and Trademark Office*